United States Patent
Kamei et al.

(10) Patent No.: US 12,290,475 B2
(45) Date of Patent: May 6, 2025

(54) UNIVERSAL LASER PROTECTIVE EYEWEAR

(71) Applicant: UNM RAINFOREST INNOVATIONS, Albuquerque, NM (US)

(72) Inventors: Masahiro Kamei, Albuquerque, NM (US); Tito Busani, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 76 days.

(21) Appl. No.: 18/194,197

(22) Filed: Mar. 31, 2023

(65) Prior Publication Data

US 2023/0320901 A1 Oct. 12, 2023

Related U.S. Application Data

(60) Provisional application No. 63/328,143, filed on Apr. 6, 2022.

(51) Int. Cl.
*A61F 9/02* (2006.01)
*A61F 9/04* (2006.01)
*G02B 27/01* (2006.01)

(52) U.S. Cl.
CPC .............. *A61F 9/022* (2013.01); *A61F 9/025* (2013.01); *A61F 9/04* (2013.01); *G02B 2027/0138* (2013.01); *G02B 27/0172* (2013.01)

(58) Field of Classification Search
None
See application file for complete search history.

(56) References Cited

U.S. PATENT DOCUMENTS

| | | | |
|---|---|---|---|
| 10,888,037 B1 * | 1/2021 | Toleno | G02B 27/0176 |
| 2016/0334644 A1 * | 11/2016 | Garofolo | G02B 27/017 |
| 2017/0007351 A1 * | 1/2017 | Yu | G02B 27/0172 |

* cited by examiner

*Primary Examiner* — Stephen T. Reed
(74) *Attorney, Agent, or Firm* — MH2 Technology Law Group LLP

(57) ABSTRACT

A laser eye protection device is described that includes an optically opaque screen that covers both eyes; one or more internal viewing screens on an eye-facing side of the optically opaque screen; and one or more cameras arranged around the optically opaque screen, wherein the one or more cameras are in electrical and data communication with the one or more internal viewing screens and provide a visual representation of surroundings to a user.

18 Claims, 3 Drawing Sheets

UNIVERSAL LASER PROTECTIVE EYEWEAR

CROSS-REFERENCE TO RELATED APPLICATIONS

This application claims priority to U.S. Provisional Application No. 63/328,143 filed on Apr. 6, 2022, the entirety of which is hereby incorporated by reference in its entirety.

FIELD

The present disclosure relates to eyewear, and in particular, to systems, devices, and method for a universal laser protective eyewear.

BACKGROUND

Typically laser safety goggles are valid only for selected wavelengths and affect visible light transmissivity through the safety goggle medium depending on their optical density, wavelength(s), and on the number of wavelengths for which they are effective. Laser wavelengths typically run from 180-10600 nm (from ultraviolet to far infrared) and optical densities run from 0 to 10, with protection increasing with higher OD numbers. For example, a pair of laser safety googles effective for the 1064 nm wavelength, a fundamental near-IR wavelength for Nd-YAG lasers (which are common) and providing an optical density (OD) of 6 may reduce visible light transmittance to 50%. A similar pair of laser safety goggles effective for a combined 800-810 nm, 940 nm, and 1064 nm that provides an OD of 7 will reduce the visible light transmittance to 30%, reducing a brightly lit room to twilight, creating secondary safety concerns based on safety equipment-induced reduced visibility. Because laser safety goggles are valid for single to several wavelengths, for those labs having multiple lasers, it is frequently necessary to have laser safety goggles specific to every laser wavelength. A given lab may have lasers with wavelengths of 355 nm, 532 nm, 795 nm, and 1064 nm. This may be covered by as few as two and as many as four pairs of laser safety goggles, dependent upon the power and type of laser (whether continuous wave or pulsed). For lasers operating in the visible spectrum (400 nm-700 nm), a highly desirable outcome is for the OD of the laser safety goggles to be only slightly higher than the calculated required OD based on laser parameters. The reason for this is that the beam may be slightly visible, which leverages the advantage available when working with visible light lasers, since it is easier to avoid a threat that one can actually use their senses to detect. If, however, the OD of the laser safety glasses is significantly higher than the required OD, then the laser beam will also be rendered invisible. Laser safety goggles for lasers operating at the 532 nm wavelength, a bright green, are available with an OD as low as 2 and providing 30% transmissivity to an OD of 10 and admitting only 16% of all visible light.

That OD of 2, however, is only effective for a 100 mW laser. A 10 W laser will require an OD of 4, which is commercially available and reduces visible light transmittance to 25%. All of these are effective in helping prevent damage to eyes, a good outcome, but at the cost of increased risk to skin damage of varying types, depending on the laser's wavelength, while aligning the laser. Goggle selection is a complicated process that requires matching goggles to requirements and having the awareness of knowing which lasers are operating prior to entering any given lab. Finally, laser safety goggles' effectiveness is affected by their condition and cleanliness. Scratched goggles are not likely to provide protection according to their specifications.

Thus, an improved laser eye protection device is needed that overcomes one or more of the above-noted deficiencies of conventional laser goggles.

SUMMARY

According to examples of the present disclosure, a laser eye protection device is disclosed. The laser eye protection comprises an optically opaque screen that covers both eyes; one or more internal viewing screens on an eye-facing side of the optically opaque screen; and one or more cameras arranged around the optically opaque screen, wherein the one or more cameras are in electrical and data communication with the one or more internal viewing screens and provide a visual representation of surroundings to a user.

In some examples, the laser eye protection can include one or more of the following feature. The optically opaque screen is opaque across a spectrum from about 180 nm to about 10,600 nm. The laser eye protection device can further comprise a power source, a communication network adaptor, and a frame that secures the optically opaque screen to the user. The communication network adaptor is a wired or wireless network adaptor. The wireless network adaptor comprises a radio frequency adaptor. The one or more internal viewing screens comprise one or more liquid crystal displays, one or more organic light emitting diodes, one or more light emitting diodes, or combinations thereof. The one or more cameras comprise six to twelve cameras. The laser eye protection device further comprises a controller that comprises a memory that stores image processing instructions that processes image signals from the one or more cameras and provides processed image signals to the one or more internal viewing screens. The controller operates with wired or wireless signals. The controller provides real time processing of the image signals that are comparable to natural human vision. The one or more internal viewing screens provides for normal human vision including peripheral vision.

According to examples of the present disclosure, a laser eye protection system is disclosed. The laser eye protection system comprises a laser eye protection device comprising: an optically opaque screen that covers both eyes; one or more internal viewing screens on an eye-facing side of the optically opaque screen; and one or more cameras arranged around the optically opaque screen, wherein the one or more cameras are in electrical and data communication with the one or more internal viewing screens and provide a visual representation of surroundings to a user; and a processing device, in data communication with the laser eye protection device, that processes data from the one or more cameras to be displayed on the one or more internal view screens.

Various additional features can be included in the laser eye protection system including one or more of the following features. The laser eye protection system further comprises a thermal sensor arranged on the optically opaque screen is opaque across a spectrum from about 180 nm to about 10,600 nm. The laser eye protection system further comprises a power source, a communication network adaptor, and a frame that secures the optically opaque screen to the user. The communication network adaptor is a wired or wireless network adaptor. The wireless network adaptor comprises a radio frequency adaptor. The one or more internal viewing screens comprise one or more liquid crystal displays, one or more organic light emitting diodes, one or more light emitting diodes, or combinations thereof. The one or more cameras comprise six to twelve cameras. The laser eye protection system further comprises a controller that comprises a memory that stores image processing instructions that processes image signals from the one or more cameras and provides processed image signals to the one or more internal viewing screens. The one or more internal viewing screens provides for normal human vision including peripheral vision.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures.

DETAILED DESCRIPTION

Figure 1B:
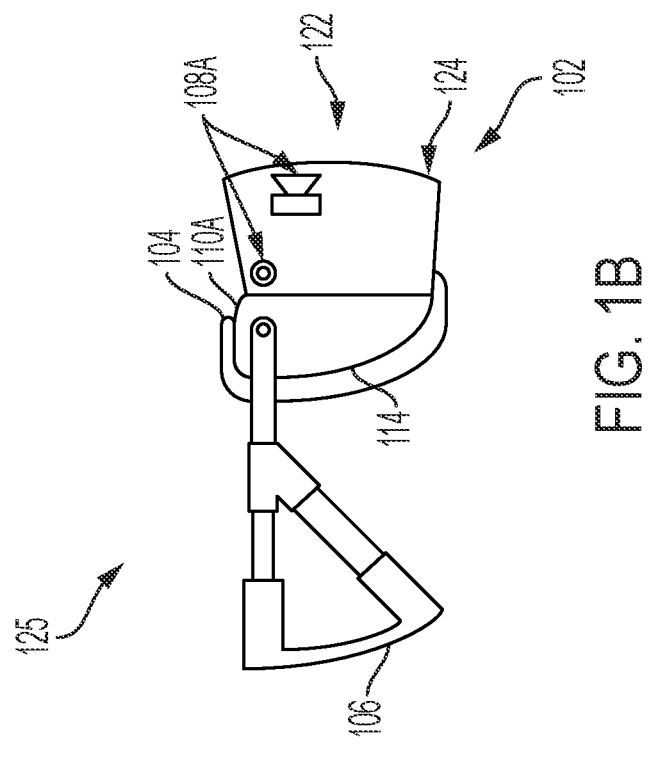
FIG. 1B shows a side view of the example shown in FIG. 1A.

Reference will now be made in detail to embodiments, examples of which are illustrated in the accompanying drawings and figures. In the following detailed description, numerous specific details are set forth in order to provide a thorough understanding of the invention. However, it will be apparent to one of ordinary skill in the art that the invention may be practiced without these specific details. In other instances, well-known methods, procedures, components, circuits and networks have not been described in detail so as not to unnecessarily obscure aspects of the embodiments.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one example" means that one or more feature, structure, or characteristic described in connection with the example is included in at least one implementation. The phrase "one example" in various places in the specification may or may not be referring to the same example.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function. Illustrative, non-exhaustive examples, which may or may not be claimed, of the subject matter according to the present disclosure are provided below.

Generally speaking, examples of the present disclosure provide for a laser eye protection device, such as laser safety goggles, to be optically opaque across all of the likely spectrum (180 nm-10600 nm) and provide internal LCD/OLED/etc. viewing screens, one for each eye, in much the same way that virtual reality (VR) headsets are made. Instead of VR, however, feed the viewing screens with actual reality processed from four cameras placed on the exterior of the safety goggles. Image processing occurs in real time and provides a field of view comparable to that of natural human vision, including peripheral vision, which may require wired communication with a controller, such as a backpack-mounted computer or similar type device, or which could also be handled by an RF (Bluetooth or WiFI) to a computer or other controller in the room.

In some examples, the laser eye protection device can include functionality for false-color imagery for regions of the spectrum not normally visible to the human eye that can further manage risk relevant to aligning UV and IR lasers, such as some shade of blue for UV and some shade of red for IR. This functionality allows risks to shift to cameras instead of human eyeballs, enables retaining the ability to see under the actual light conditions within any given room, and is effective for all laser wavelengths, power levels, and types.

Figure 1A:
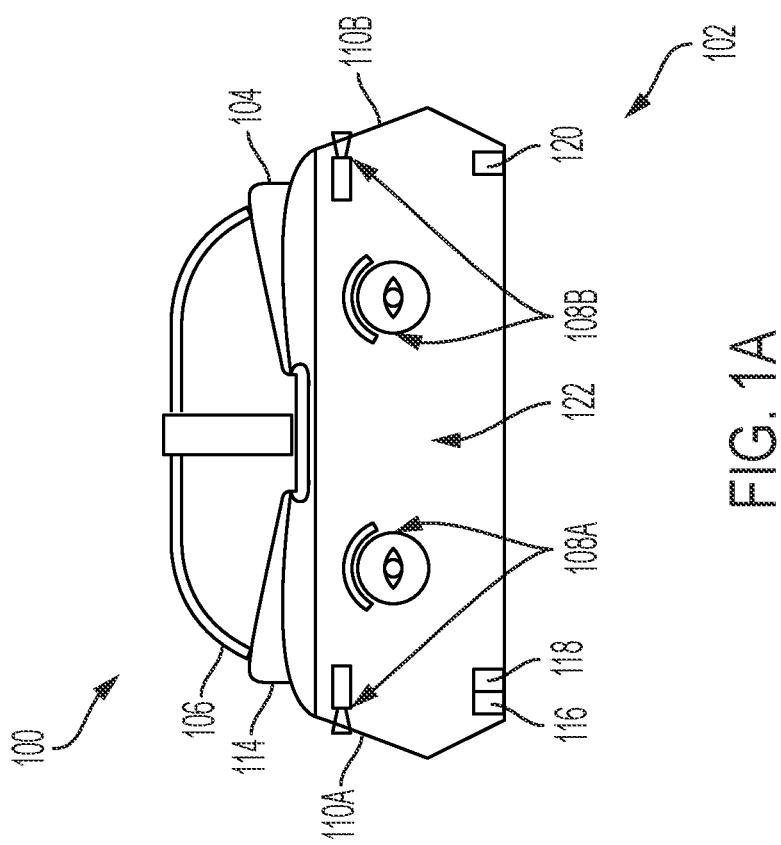
FIG. 1A shows a front view of an eye protection device according to examples of the present disclosure.
Figure 1C:
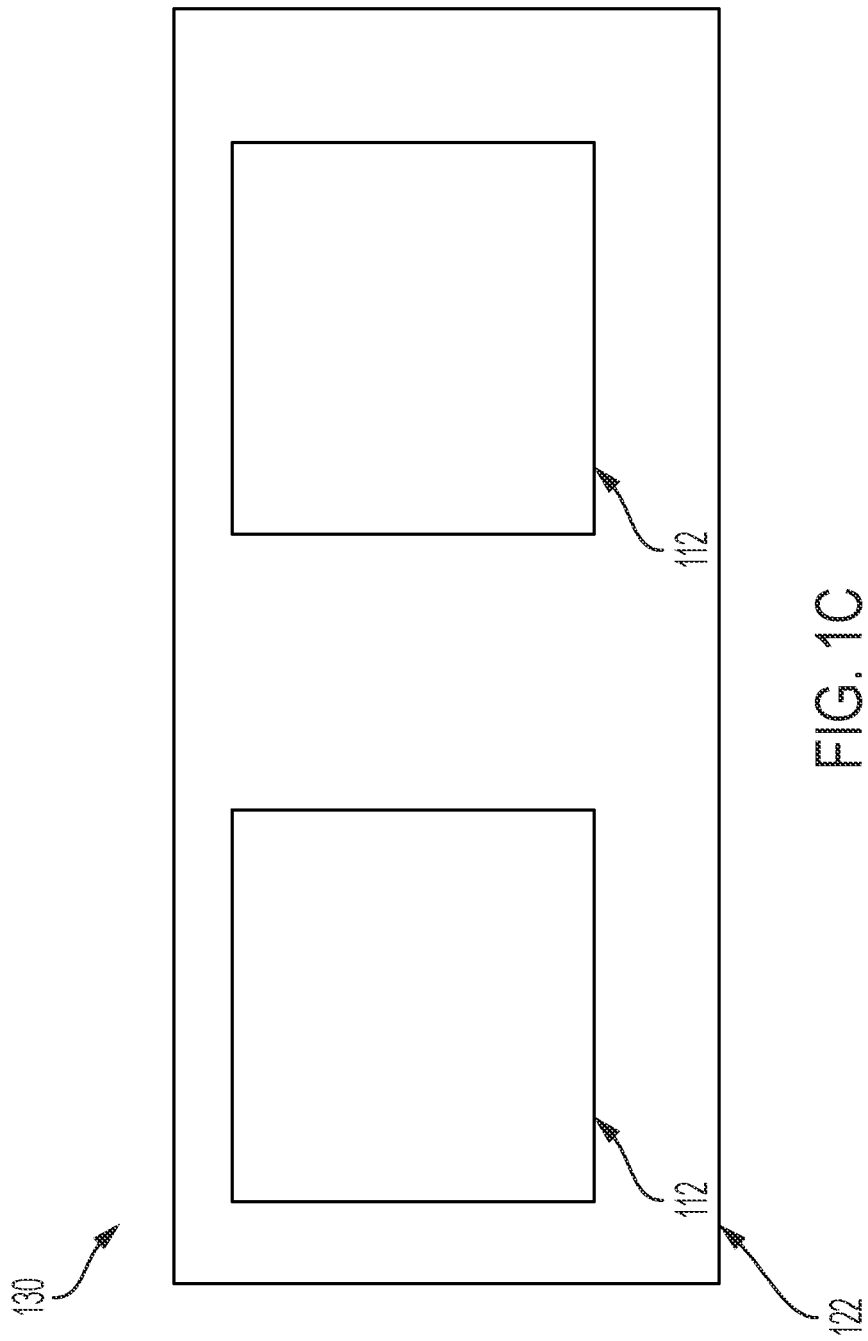
FIG. 1C shows a simplified rear view (user-facing side) of the example shown in FIG. 1A.

FIG. 1A shows a front view of an eye protection device 100 according to examples of the present disclosure. FIG. 1B shows a side view of the eye protection device 125 of the example shown in FIG. 1A. Front view of an eye protection device 100 and side view of the eye protection device 125 comprises optically opaque screen 102 that covers both eyes. In one non-limiting example optically opaque screen 102 can comprise a steel surface, such as a ⅛ steel surface, or other suitably optically opaque material(s). In some examples, optically opaque screen 102 is opaque across a spectrum from about 180 nm to about 10,600 nm. FIG. 1C shows a simplified rear view (user-facing side) 130 of the example shown in FIG. 1A. The eye protection device comprises one or more internal viewing screens 112 on an eye-facing side of optically opaque screen 102. The eye protection device comprises one or more cameras 108A, 108B, 110A, 110B arranged around optically opaque screen 102. As shown in FIG. 1A and FIG. 1B, the cameras 108A and 108B are positioned around the location of the user's eyes, where camera 108A is arranged in front of the right eye and camera 108B is arranged in front of the left eye (from the perspective of viewing out of the document). As shown in FIG. 1A and FIG. 1B, the cameras 110A and 110B are positioned around the periphery of the user's eyes, where camera 110A is arranged at the periphery of the right eye and camera 110B is arranged at the periphery of the left eye (from the perspective of viewing out of the document). The one or more cameras 108A, 108B, 110A, 110B are in electrical and data communication with the one or more internal viewing screens 112 and provide a visual representation of surroundings to a user.

The eye protection device can further comprise a power source 116 and a communication network adaptor 118. The features of the eye protection device can be supported by frame 114 that can be secured to the head of the user using back head strap 106. Communication network adaptor 118 is a wired or wireless network adaptor. The wireless network adaptor comprises a radio frequency adaptor. The one or more internal viewing screens 114 can comprise one or more liquid crystal displays, one or more organic light emitting diodes, one or more light emitting diodes, or combinations thereof. The one or more cameras comprise 108A, 108B, 110A, 110B can comprise a number of separate cameras, such as six to twelve cameras in one non-limiting example. The eye protection device further comprises controller 120 that comprises a memory that stores image processing instructions that processes image signals from the one or more cameras and provides processed image signals to the one or more internal viewing screens. Controller 120 operates with wired or wireless signals. Controller 120 provides real time processing of the image signals that are comparable to natural human vision. The one or more internal viewing screens 114 provides for normal human vision including peripheral vision.

In some examples, the eye protection device can further comprise one or more thermal sensors and one or more thermal detectors 124. The one or more thermal sensors and one or more thermal detectors 124 can be integrated into the optically opaque screen 102 or the lens 122 of the eye protection device as a separate film, material, composition, or layer of the lens material on either the outward facing side or inward facing side of the optically opaque screen 102 or the lens 122. The one or more thermal sensors and one or more thermal detectors 124 can comprise a thermal sensor arranged on the optically opaque screen is opaque across a spectrum from about 180 nm to about 10,600 nm. In one non-limiting example, the one or more thermal sensors and one or more thermal detectors 124 can be based on a black-body radiation-based IR semiconductor-based detector, such as Ge or similar type semiconductor materials, to measure the temperature of a body. In another non-limiting example, the one or more thermal sensors and one or more thermal detectors can be based on a change of the resistivity of a small filament, such as Pt, that is linearly proportional to the temperature. In some examples, the one or more thermal sensors and one or more thermal detectors 124 can include a flexible micro-three-dimensional sensor, with a combination of platinum and indium oxide to form thermocouples, that is designed and fabricated by a microfabrication process to achieve in situ real-time temperature measurements. In some examples, the one or more thermal sensors and one or more thermal detectors 124 can include sacrificial Phase Change Material (PCM) materials that change phase from gel to rigid solid state once the environmental temperature is above to a certain point, i.e. a safety point. The PCM in gel form can be contained in a small glass membrane that protect the "eyes" of the safety google. The phase change will induce a volume increases and so a crack of the small glass membrane. A small noise induced by the crack will be detected by a noise detector or just visually from the google cameras. The PCM in gel form is a cost-effective approach, however the PCM would need to changed once it has changed phase from gel to solid. In another example the one or more thermal sensors and one or more thermal detectors 124 can include the use of shape memory materials that can recover their initial gel state once the temperature decreases.

Figure 2:
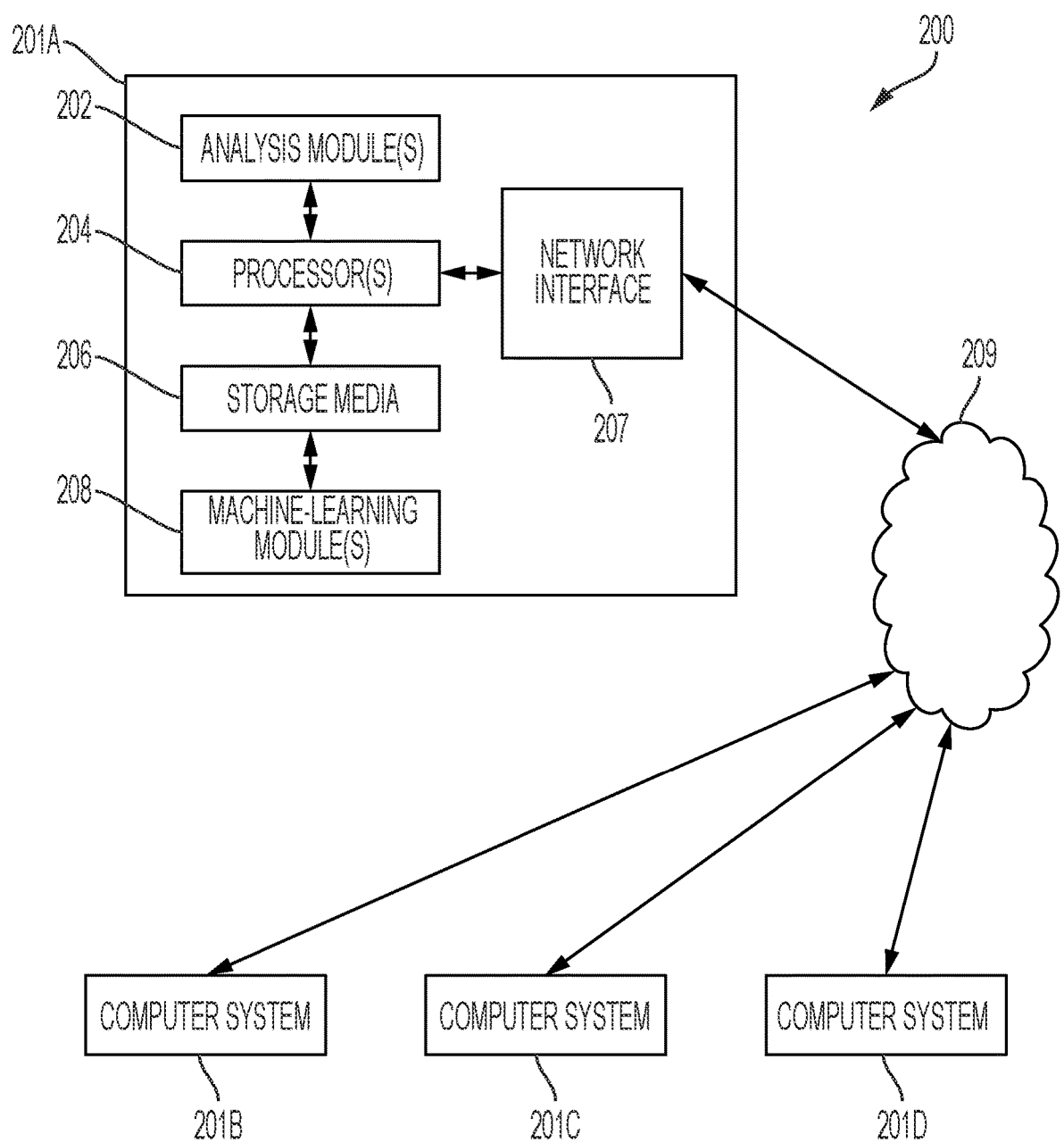
FIG. 2 illustrates an example of a computing system in accordance with some embodiments.

In some examples, one or more features and/or functionalities of the eye protection device according to examples of the present disclosure may be executed by and/or in combination with functionality of a computing system using, for example, network adaptor 118 and/or controller 120. FIG. 2 illustrates an example of such a computing system 200, in accordance with some embodiments. The computing system 200 may include a computer or computer system 201A, which may be an individual computer system 201A or an arrangement of distributed computer systems. The computer system 201A includes one or more analysis module(s) 202 configured to perform various tasks according to some embodiments, such as one or more methods disclosed herein. To perform these various tasks, the analysis module 202 executes independently, or in coordination with, one or more processors 204, which is (or are) connected to one or more storage media 206. The processor(s) 204 is (or are) also connected to a network interface 207 to allow the computer system 201A to communicate over a data network 209 with one or more additional computer systems and/or computing systems, such as 201B, 201C, and/or 201D (note that computer systems 201B, 201C and/or 201D may or may not share the same architecture as computer system 201A, and may be located in different physical locations, e.g., computer systems 201A and 201B may be located in a processing facility, while in communication with one or more computer systems such as 201C and/or 201D that are located in one or more data centers, and/or located in varying countries on different continents). A processor can include a microprocessor, microcontroller, processor module or subsystem, programmable integrated circuit, programmable gate array, or another control or computing device.

The storage media 1906 can be implemented as one or more computer-readable or machine-readable storage media. The storage media 206 can be connected to or coupled with a neuromodulation machine learning module(s) 208. Note that while in the example embodiment of FIG. 2 storage media 206 is depicted as within computer system 201A, in some embodiments, storage media 206 may be distributed within and/or across multiple internal and/or external enclosures of computing system 201A and/or additional computing systems. Storage media 206 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLURAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions or located at a remote site from which machine-readable instructions can be downloaded over a network for execution.

It should be appreciated that computing system 200 is only one example of a computing system, and that computing system 200 may have more or fewer components than shown, may combine additional components not depicted in the example embodiment of FIG. 2, and/or computing system 200 may have a different configuration or arrangement of the components depicted in FIG. 2. The various components shown in FIG. 2 may be implemented in hardware, software, or a combination of both hardware and software, including one or more signal processing and/or application specific integrated circuits.

Further, the steps in the processing methods described herein may be implemented by running one or more functional modules in an information processing apparatus such as general purpose processors or application specific chips, such as ASICs, FPGAs, PLDs, or other appropriate devices. These modules, combinations of these modules, and/or their combination with general hardware are all included within the scope of protection of the invention.

Vision models and/or other interpretation aids may be refined in an iterative fashion; this concept is applicable to embodiments of the present methods discussed herein. This can include use of feedback loops executed on an algorithmic basis, such as at a computing device (e.g., computing system 2000, FIG. 20), and/or through manual control by a user who may make determinations regarding whether a given step, action, template, model, or set of curves has become sufficiently accurate for the evaluation of the signal(s) under consideration.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. Moreover, the order in which the elements of the methods are illustrated and described may be re-arranged, and/or two or more elements may occur simultaneously. The embodiments were chosen and described in order to best explain the principles of the invention and its practical applications, to thereby enable others skilled in the art to best utilize the invention and various embodiments with various modifications as are suited to the particular use contemplated.

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus(es) and method(s) disclosed herein in any combination, and all of such possibilities are intended to be within the scope of the present disclosure.

Many modifications of examples set forth herein will come to mind to one skilled in the art to which the present disclosure pertains having the benefit of the teachings presented in the foregoing descriptions and the associated drawings. Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

What is claimed is:

1. A laser eye protection device comprising:
    an optically opaque screen that covers both eyes;
    one or more internal viewing screens on an eye-facing side of the optically opaque screen;
    a thermal sensor arranged on the optically opaque screen; and
    one or more cameras arranged around the optically opaque screen, wherein the one or more cameras are in electrical and data communication with the one or more internal viewing screens and provide a visual representation of surroundings to a user,
    wherein the optically opaque screen is opaque across a spectrum from about 180 nm to about 10,600 nm.

2. The laser eye protection device of claim 1, further comprising a power source, a communication network adaptor, and a frame that secures the optically opaque screen to the user.

3. The laser eye protection device of claim 2, wherein the communication network adaptor is a wired or wireless network adaptor.

4. The laser eye protection device of claim 3, wherein the wireless network adaptor comprises a radio frequency adaptor.

5. The laser eye protection device of claim 1, wherein the one or more internal viewing screens comprise one or more liquid crystal displays, one or more organic light emitting diodes, one or more light emitting diodes, or combinations thereof.

6. The laser eye protection device of claim 1, wherein the one or more cameras comprise six to twelve cameras.

7. The laser eye protection device of claim 1, further comprising a controller that comprises a memory that stores image processing instructions that processes image signals from the one or more cameras and provides processed image signals to the one or more internal viewing screens.

8. The laser eye protection device of claim 7, wherein the controller operates with wired or wireless signals.

9. The laser eye protection device of claim 7, wherein the controller provides real time processing of the image signals that are comparable to natural human vision.

10. The laser eye protection device of claim 1, wherein the one or more internal viewing screens provides for normal human vision including peripheral vision.

11. A laser eye protection system comprising:
    a laser eye protection device comprising:
        an optically opaque screen that covers both eyes;
        one or more internal viewing screens on an eye-facing side of the optically opaque screen;
        a thermal sensor arranged on the optically opaque screen; and
        one or more cameras arranged around the optically opaque screen, wherein the one or more cameras are in electrical and data communication with the one or more internal viewing screens and provide a visual representation of surroundings to a user; and
    a processing device, in data communication with the laser eye protection device, that processes data from the one or more cameras to be displayed on the one or more internal view screens, wherein the optically opaque screen is opaque across a spectrum from about 180 nm to about 10,600 nm.

12. The laser eye protection system of claim 11, further comprising a power source, a communication network adaptor, and a frame that secures the optically opaque screen to the user.

13. The laser eye protection system of claim 12, wherein the communication network adaptor is a wired or wireless network adaptor.

14. The laser eye protection system of claim 13, wherein the wireless network adaptor comprises a radio frequency adaptor.

15. The laser eye protection system of claim 11, wherein the one or more internal viewing screens comprise one or more liquid crystal displays, one or more organic light emitting diodes, one or more light emitting diodes, or combinations thereof.

16. The laser eye protection system of claim 11, wherein the one or more cameras comprise six to twelve cameras.

17. The laser eye protection system of claim 11, further comprising a controller that comprises a memory that stores image processing instructions that processes image signals from the one or more cameras and provides processed image signals to the one or more internal viewing screens.

18. The laser eye protection system of claim 11, wherein the one or more internal viewing screens provides for normal human vision including peripheral vision.

* * * * *